United States Patent
Rosa et al.

[11] Patent Number: 5,618,441
[45] Date of Patent: Apr. 8, 1997

[54] SINGLE MICROCONTROLLER EXECUTION OF CONTROL AND SAFETY SYSTEM FUNCTIONS IN A DIALYSIS MACHINE

[76] Inventors: Jim Rosa, 11183 Conifer Mountain Rd., Conifer, Colo. 80433; Steve Love, 314 Bluebird Dr., Bailey, Colo. 80421; Preben A. Peterson, Rue Rollebeek 40, 1000 Bruxelles, Belgium; Antonio Bosetto, Via Ippolito Nievo 18/A, 41037 Mirandola (Modena), Italy

[21] Appl. No.: 483,456

[22] Filed: Jun. 7, 1995

[51] Int. Cl.$^6$ ................................................ B01D 61/32
[52] U.S. Cl. ...................... 210/739; 210/143; 210/646; 395/924; 395/497.04; 604/4
[58] Field of Search ............................... 210/85, 138, 143, 210/646, 739, 929; 604/4–6; 364/413.01, 413.02, 413.07; 395/140, 155, 160, 161, 924, 156, 480, 497.04

[56] References Cited

U.S. PATENT DOCUMENTS

| | | | |
|---|---|---|---|
| 4,167,663 | 11/1979 | Granzow, Jr. et al. | 219/497 |
| 4,370,983 | 2/1983 | Lichtenstein | 210/929 |
| 4,389,640 | 6/1983 | Dawdy | 340/664 |
| 4,628,186 | 12/1986 | Bergemann et al. | 219/497 |
| 4,725,694 | 2/1988 | Auer et al. | 178/18 |
| 4,756,706 | 7/1988 | Kerns et al. | 604/66 |
| 4,796,634 | 1/1989 | Huntsman et al. | 128/662.01 |
| 4,990,258 | 2/1991 | Bjare et al. | 210/647 |
| 5,053,684 | 10/1991 | Nooyen | 315/392 |
| 5,189,609 | 2/1993 | Tivig et al. | |
| 5,276,611 | 1/1994 | Ghiraldi | |
| 5,319,363 | 6/1994 | Welch et al. | 340/825.36 |
| 5,326,476 | 7/1994 | Grogan et al. | 210/646 |
| 5,472,614 | 12/1995 | Rossi | 210/646 |
| 5,486,286 | 1/1996 | Peterson et al. | 210/87 |
| 5,487,827 | 1/1996 | Peterson et al. | 210/87 |

FOREIGN PATENT DOCUMENTS

| | | |
|---|---|---|
| 0428505A | 5/1991 | European Pat. Off. . |
| 0432138A2 | 6/1991 | European Pat. Off. . |
| 9014850 | 12/1990 | WIPO . |

OTHER PUBLICATIONS

"AK–10 System Operator's Manual for Hemofiltration" by Gambro, Undated.
"Microcomputers in Safety Technique: An Aid to Orientation for Developer and Manufacturer", by Bayern and Rheinland, Results of a Research Report., Undated.

*Primary Examiner*—Joseph W. Drodge
*Attorney, Agent, or Firm*—John R. Ley

[57] ABSTRACT

A dialysis machine uses a single microcontroller to perform both safety system functions and control system functions. A single segmented memory records the safety system code and data separately and in isolation from the control system code and data. Access to the safety system software is limited to the operating system and safety system contexts. A protected mode of operation of an embedded processor allows recovery of a state vector upon failures of the operating system, the safety system and the control system. The operating system allows recovery of a state vector upon failure of the safety system and the operating system. A watchdog timer circuit places the dialysis machine in a safe patient state if a total failure of the microcontroller occurs. This functionality assures that the machine is placed in safe patient state under failure conditions and that the safety system software is isolated from the control system software to avoid having to re-validate the safety system when control system software changes are made.

16 Claims, 5 Drawing Sheets

SINGLE MICROCONTROLLER EXECUTION OF CONTROL AND SAFETY SYSTEM FUNCTIONS IN A DIALYSIS MACHINE

The present invention relates to a new and improved dialysis machine and method of controlling a dialysis machine in which a single microcontroller, microprocessor or other computer or processor device, any of which are hereafter referred to as a "microcontroller," effectively performs both the control system and the safety system functions of the machine in a safe and reliable manner and in accordance with commonly accepted safety standards.

CROSS REFERENCE TO RELATED APPLICATIONS

The subject matter disclosed in a U.S. patent application for an Information Entry Validation System And Method For A Dialysis Machine, Ser. No. 08/484,015 filed concurrently therewith is incorporated in this application by reference.

BACKGROUND OF THE INVENTION

In general, a dialysis machine is used as a substitute for the natural kidney functions of a human body. As such, the dialysis machine cleanses the blood of the natural accumulation of bodily wastes and separates the wastes from the blood outside of or extracorporeally of the body. The separated wastes are discharged, and the cleansed blood is returned to the body.

The wastes are separated from the blood in a dialyzer. The dialyzer includes an internal housing which is separated by a porous membrane into a blood side or compartment and a dialysate side or compartment. The blood removed from the patient flows through the blood side of the dialyzer. A prepared solution of dialysate is passed through the dialysate side of the dialyzer. The wastes from the blood pass through the membrane by osmosis, ionic transfer or fluid transport into the dialysate and, depending upon the type of dialysis treatment, desirable components from the dialysate may pass in the opposite direction through the membrane and into the blood. The transfer of the wastes into the dialysate cleanses the blood while allowing the desired components from the dialysate to enter the bloodstream.

As is apparent, the dialysis machine must be properly operated to perform effective dialysis in a safe and reliable manner. With the patient's blood being removed and passed through an extracorporeal flow path, care must be taken that the blood is not contaminated and is handled safely. The dialysate, which flows in a hydraulics flow path, must be controlled in both composition and physical characteristics. The mixture of components in the dialysate must also be correct and safe. The ability to clean the hydraulics flow path prior to use is essential to avoid the possibility of introducing undesirable microorganisms into the blood.

In addition to controlling the operational functions, the functionality of the dialysis machine and the condition of the patient must be monitored for safety or protective purposes. For example, the condition and integrity of the dialyzer medium must be monitored to detect a failure which would allow the dialysate to directly enter the blood and to detect any obstruction which would inhibit or terminate the flow of wastes from the blood across the membrane and into the dialysate. Monitoring certain bodily functions of the patient allows the early detection of a potentially risky condition developing in the patient during treatment.

Modern dialysis machines incorporate a large number of safety or protective features in a safety system, because of the potential for serious consequences resulting from a system failure or unsafe patient condition. The safety system includes sensors located in the extracorporeal and hydraulics flow paths to derive signals representative of the operating conditions or parameters. From these sensor signals the safety system evaluates safety conditions of the machine and the patient. In addition, all known dialysis machines employ separate and distinct safety and control system microcontrollers to separately execute the safety and the normal operating functions of the dialysis machine. A safety system microcontroller executes the safety functions based on signals from the sensors and its own software program, and a separate control system microcontroller executes the normal operating control functions based on the signals from the sensors and its own separate software program.

Upon recognizing a safety or risk condition, the safety system microcontroller places the dialysis machine in a safe state to prevent or greatly reduce the risk of injury to the patient. Under such conditions the safety microcontroller overrides any commands delivered by the control system microcontroller. So long as a safety or risk condition is not detected, the safety microcontroller exercises little or no control but instead allows the control system microcontroller to exercise normal control over the operation of the dialysis machine. The control system microcontroller thus assures that the dialysis treatment will proceed as the operator has selected, under normal conditions. Thus, the control system microcontroller exercises control over the normal operating functionality, and the safety system microcontroller exercises the ultimate and predominant control over the entire dialysis machine in safety and protective situations.

In large measure, the use of the two separate control system and safety system microcontrollers is as a result of the relatively stringent standards established by health and safety and governmental groups. These standards have required that the dialysis machine respond to catastrophic and lesser forms of failure by placing the patient in a safe condition despite the failure. The two-microcontroller approach satisfies these standards due to the redundancy of control by both the safety system and control system microcontrollers. If a failure occurs in the control system microcontroller, the safety system microcontroller assures that the necessary safety and protective state will be achieved. If a failure occurs in the safety system microcontrollers, the control system microcontroller is capable of exercising adequate control over the system to maintain a safe state.

Furthermore by maintaining the safety and control functionality in separate software, changes in control system functionality can be made without adversely affecting the safety system software. The separated safety system and control system software also satisfies an additional provision of the safety standards which specifies that an actual or potential change to the safety system software will require re-validation of the safety system functionality. Re-validation is a process during which the functionality of the safety system must be demonstrated and confirmed as safe. Re-validation is a time consuming and expensive task, so the separate division of the control system software from the safety system software avoids the possibilities and costs associated with having to re-validate the safety system.

As a consequence of the practical considerations and the relevant safety standards described briefly above, all known prior dialysis machines have followed the two separate microcontroller systems approach. With the advent of stricter governmental and other economic controls over the costs of medical equipment and treatments, especially those regularly recurring treatments of significant cost such as dialysis treatments, considerable emphasis has been placed on reducing treatment costs. A portion of the treatments cost is attributable to the costs of the dialysis machine and its maintenance. It is therefore desirable to reduce costs associated with the purchase and maintenance of dialysis machines as one approach to reducing the costs and expenses of dialysis treatments.

These and other considerations have contributed to the evolution of the present invention which is summarized below.

SUMMARY OF THE INVENTION

One of the significant aspects of the present invention pertains to the use of a single microcontroller in a dialysis machine to safely obtain both the control system and safety system functionality in a manner which is safe to the patient and which complies with the appropriate governmental and safety standards which govern dialysis machines. Another significant aspect of the present invention relates to the reduction in cost of dialysis machines by use of a single microcontroller which accomplishes the control system and safety system functionality of a dialysis machine, without compromising patient safety or governmental and safety regulations. A further significant aspect of the present invention relates to the use of a single memory bank within a dialysis machine which contains the control system software and the safety system software in such a manner that the safety system software is not compromised if a failure in the control system functionality occurred. Still another significant aspect of the present invention relates to isolating or separating the control system software from the safety system software in a single memory of a dialysis machine in such a manner to avoid the necessity to re-validate the safety system when changes are made to the control system software.

In accordance with these and other aspects, the present invention may be generally summarized as a dialysis machine having a single microcontroller which performs safety system functions and control system functions during dialysis treatments. Preferably a single segmented memory is connected to the single microcontroller in which instructional code for the safety system functions is recorded separately and in isolation from the code for the control system and other functions. The code for the safety system functions can be accessed only from the context of the microcontroller performing safety system control functions.

A protected mode of operation for the microcontroller is also preferably employed. The protected mode of operation allows recovery and entry into the safety system software from a failure occurring when the control system functions are performed. Recovery into the safety system functions allows the machine to be placed in a safe patient condition. The safety regulations pertaining to recovery into the safe patient state are thereby satisfied using only a single microcontroller.

By isolating the instructional code for the safety system control functions in the segmented memory and allowing access to the safety system code and data only from a safety system context, the safety system code is insulated from changes which might occur inadvertently during operation in the control system context. The extensive and time consuming problem of re-validating the safety system is thereby avoided by use of a segmented memory.

A watchdog timer circuit is preferably connected to the microcontroller to continually monitor its functionality and to detect its failure. The watchdog timer circuit acts on its own without the microcontroller to place the dialysis machine into a safe patient condition upon detection of failure of the single microcontroller. The watchdog timer circuit thereby provides protection against the total failure of the microcontroller.

The instructional code for the microcontroller is also organized in a hierarchy of privilege. The safety system code and data are accessible only from the operating system and safety system contexts. The safety system always has access to the control system software to place the dialysis machine into the safe patient state independent of the status or functionality of the control system software. The control system does not have the privilege to, and therefore can not access, the safety system software, thus preventing corruption of the safety system during normal execution of the controls system functions of the dialysis machine.

The privilege hierarchial arrangement always allows a recovery to the safety system, so that a safe patient state can be acheived after an error in the execution of the control system or the operating system functionality. The hierarchical arrangement of privilege further contributes to the maintenance of the safety system while permitting adequate control system functionality.

A more complete appreciation of the present invention and its scope may be obtained from the accompanying drawings, which are briefly summarized below, from the following detail descriptions of presently preferred embodiments of the invention, and from the appended claims.

DETAILED DESCRIPTION

Figure 1:
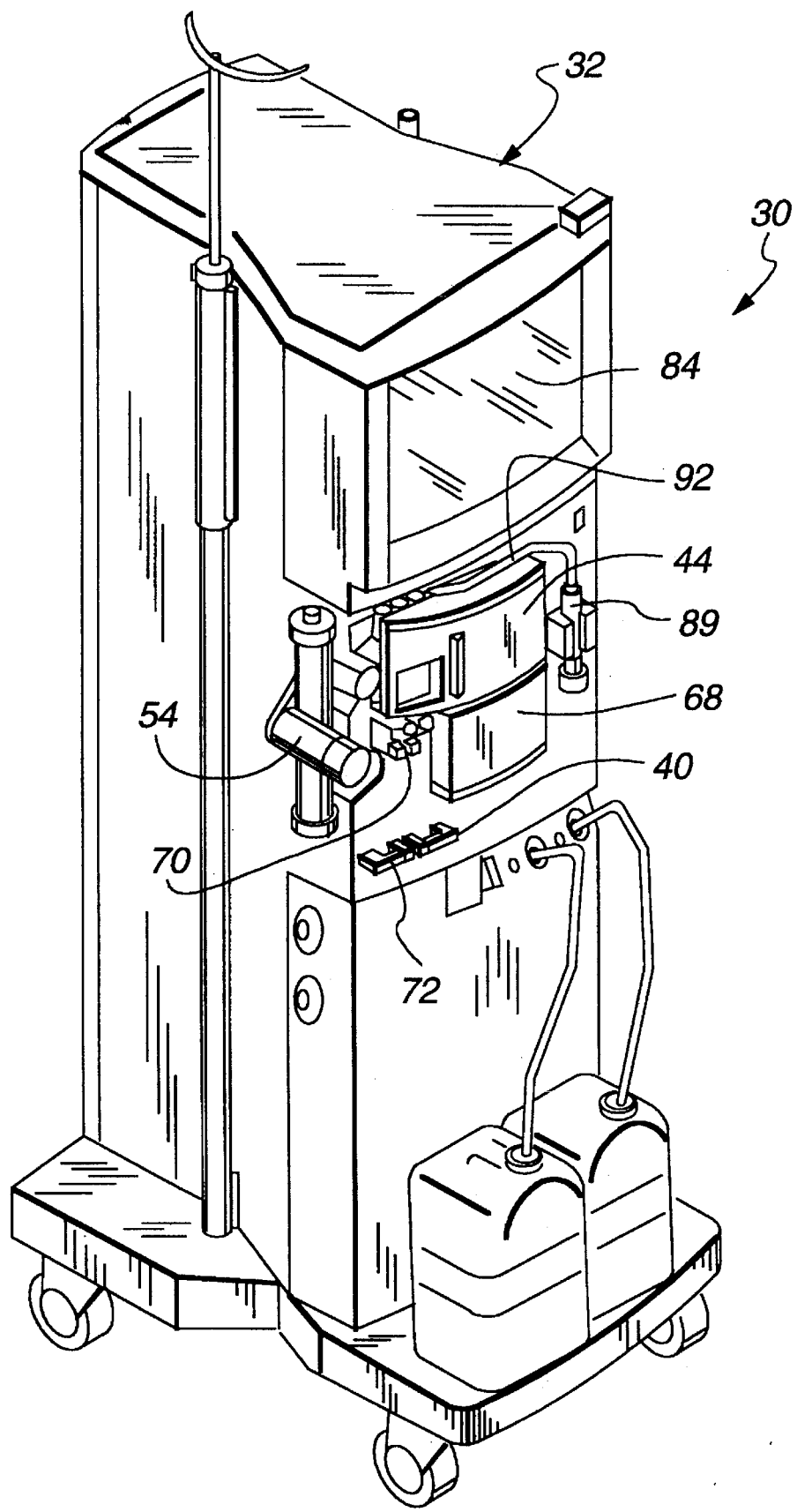
FIG. 1 is a perspective view of a dialysis machine which incorporates the present invention.

An example of a dialysis machine with which the present invention may be advantageously employed is shown at 30 in FIG. 1. The dialysis machine 30 includes an enclosure 32 to which or within which there are housed those functional devices and components of the dialysis machine generally illustrated in FIG. 2.

Figure 2:
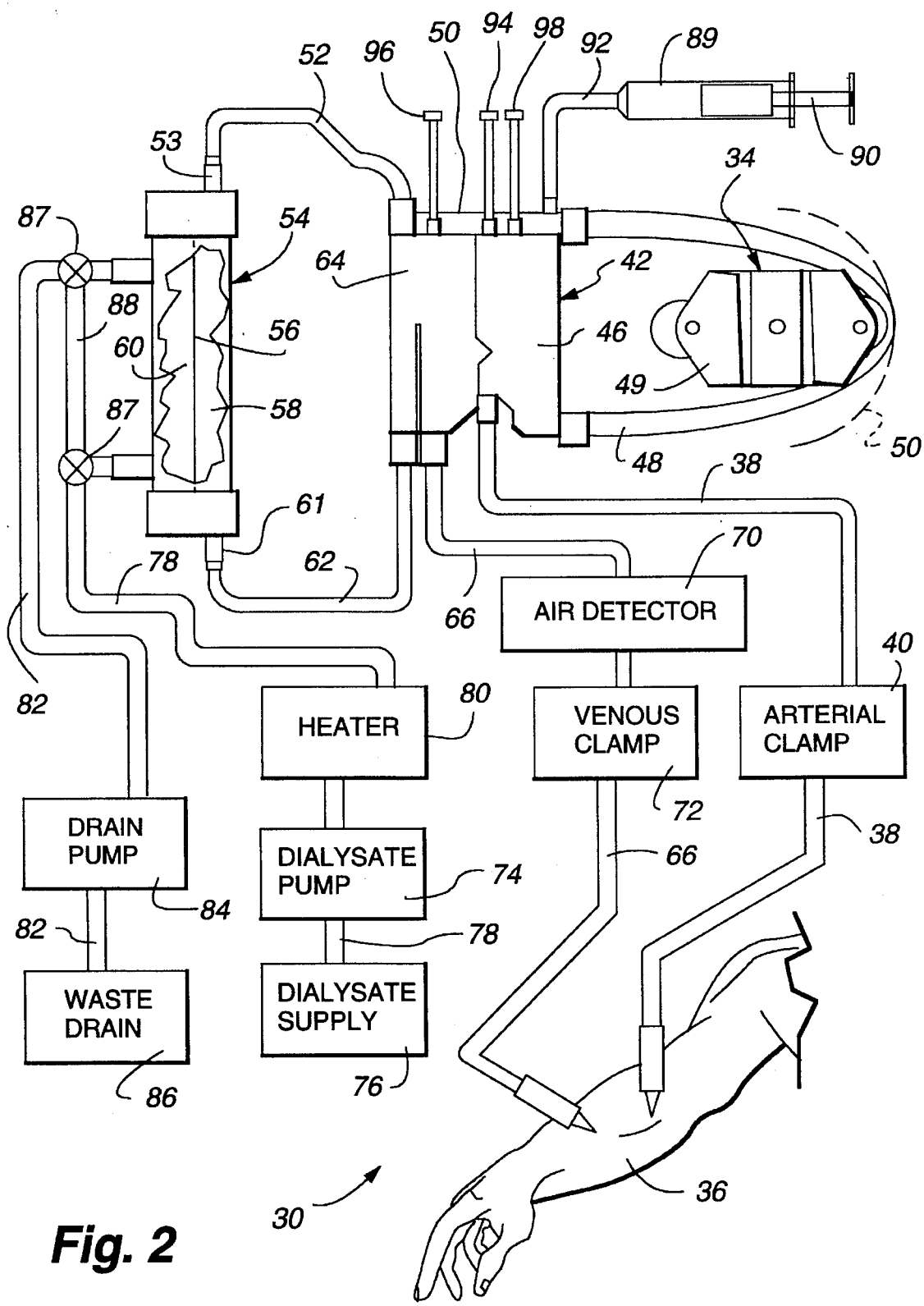
FIG. 2 is a generalized view illustrating a dialyzer, an extracorporeal blood flow path through the dialyzer, and a hydraulics flow path through the dialyzer, which exist during use of the dialysis machine shown in FIG. 1.

The dialysis machine 30 includes at least one blood pump 34 which controls the flow of blood from a patient 36, as shown in FIG. 2. An arterial line or tubing 38 is connected through an arterial clamp 40 to a blood handling cartridge 42. The blood handling cartridge 42 is normally retained behind a door 44 of the machine 30 when used. The blood handling cartridge 42 is not shown in FIG. 1. The blood pump 34 also is located behind the door 44 and adjacent to the cartridge 42. The blood pump 34 is typically a peristaltic pump in dialysis machines.

Blood from the patient 36 flows through an extracorporeal flow path when the blood pump 34 draws blood from the patient 36 through the arterial line 38 and into an arterial chamber 46 of the cartridge 42. The blood pump 34 draws blood from the arterial chamber 46 through a pump tubing 48 which is squeezed or pinched by a rotating rotor 49 against a stationary raceway 50, in the typical manner of peristaltic pumps. The blood within the pump tubing 48 which is rotationally in front of the rotor 49 is propelled through the pump tubing 48 and into a manifold 50 of the cartridge 42. A tubing 52 conducts the blood from the manifold 50 of the cartridge into a blood inlet 53 of a conventional dialyzer 54. A micro-porous or other type of dialysis medium 56 divides the interior of the dialyzer 54 into a blood chamber 58 and a dialysate chamber 60.

While in the dialyzer 54, the waste products from the patient 36 are separated from the blood, and the cleansed blood is transferred through an outlet 61 in a tubing 62 back to an inlet of a venous chamber 64 of the cartridge 42. Any air which might have been unintentionally introduced into the blood is collected and removed while in the venous chamber 64.

Blood from the venous chamber 64 is removed from the cartridge 42 through a venous tubing or line 66. Although not shown in FIG. 2, a venous blood pump similar to the arterial blood pump 34 may be located along the venous line 66 to assist in forcing the blood back into the patient 36. If employed, the venous blood pump is positioned behind a second door 68 as shown in FIG. 1.

The venous blood pump is operated at a lesser volumetric pumping rate compared to the volumetric pumping rate of the arterial blood pump 34 when it is desired to transfer components from the blood by fluid transport through the medium 56 into the dialysate chamber 60 of the dialyzer 54. The venous blood pump is operated at a greater volumetric pumping rate compared to the volumetric pumping rate of the arterial blood pump 34 when it is desired to draw fluid components by fluid transport from the dialysate chamber 60 into the bloodstream of the patient 36. Both of these flow control techniques are well known ultrafiltration dialysis treatments.

After leaving the venous chamber 64 the blood flows through the venous line 66 to an air detector 70. The air detector 70 derives signals related to the quantity of air, if any, remaining in the venous line 66. If an excessive or dangerous amount of air is present, a safety control signal will be generated and a venous line clamp 72 will immediately close to terminate the flow of blood through the venous line 66 before the air reaches the patient 36.

The enclosure 32 (FIG. 1) of the dialysis machine 30 also encloses the various elements of a hydraulics flow path, which is shown in abbreviated form in FIG. 2. The elements of the hydraulics flow path include a number of different valves (most of which are not shown) and a dialysate pump 74 which draws dialysate from a container 76 or from an internal supply of dialysate which the dialysis machine 30 has prepared from appropriate chemicals and a supply of purified water.

The dialysate pump 74 draws the dialysate from the supply 76 and delivers the dialysate through a dialysate supply tubing or line 78 to a dialysate inlet of the dialysate chamber 60 of the dialyzer 54. The dialysate flows past the medium 56 where it absorbs the waste products from the blood in the blood chamber 58. Any beneficial components within the dialysate which are desired to be transferred to the blood pass through the medium 56 and into the blood in the blood chamber 58.

Prior to entering the dialyzer 54, the dialysate is heated in a heater 80 to the normal human body temperature. Because the dialysate and the blood will readily transfer heat within the dialyzer 54, it is important that the dialysate be at body temperature. Otherwise, potentially damaging effects on the patient could result from excessive heat transfer to the patient or away from the patient. Furthermore, the transferred heat from excessively hot dialysate will kill blood cells. Temperature sensors (not shown) are located in the dialysate supply line 78 to detect excessively warm dialysate entering the dialyzer 54.

Conductivity sensors (not shown) are also present in the dialysate supply line 78 to measure the conductivity of the dialysate. Predetermined conductivity characteristics of the dialysate are frequently necessary to achieve the desired level of ionic transfer between the blood and the dialysate.

Dialysate containing the waste products is removed from the dialysate chamber 60 through a dialysate waste tubing or line 82 by operation of a drain pump 84. The drain pump 84 is operated at a lesser volumetric pumping rate compared to the volumetric pumping rate of the dialysate pump 74 when it is desired to transfer components from the dialysate by fluid transport into the blood in the dialyzer 54. The drain pump 84 is operated at a greater volumetric pumping rate compared to the volumetric pumping rate of the dialysate pump 74 when it is desired to remove fluid components from the blood by fluid transport. Both of these flow control techniques are well known dialysis treatments.

The dialysate removed from the dialyzer 54 is delivered by the drain pump 84 to a waste drain 86. The waste drain 86 may be a separate container which accumulates the used dialysate and accumulated waste products, or it may simply be a public sewer.

As a safety measure to reduce the potentially dangerous effects of a malfunction in the hydraulics flow path, bypass valves 87 are positioned at the inlet and the outlet of the dialysate chamber 60. The bypass valves 87 are connected by a bypass line 88. Normally the bypass valve 87 at the inlet to the dialysate chamber 60 directs the dialysate in the dialysate supply line 78 into the dialysate chamber. Similarly the bypass valve 87 at the outlet of the dialysate chamber 60 directs the exiting dialysate into the dialysate waste line 82. However, should a malfunction be detected, the bypass valves 87 will be operated to their alternative state. In the alternative state, the valves 87 connect the dialysate supply line 78 to the dialysate waste line 82, thereby bypassing the dialyzer 54 with the flow of dialysate. This bypass condition prevents the further interaction of the dialysate with the blood in the dialyzer, and the bypass condition can be achieved upon the occurrence of a safety condition.

Because the blood and the extracorporeal flow path is prone to clot, it is typical to inject an anticoagulant such as heparin into the extracorporeal flow path. The typical approach to injecting the anticoagulant is to slowly deliver it from a syringe 89. A plunger 90 of the syringe is slowly and controllably displaced into the syringe 89 by a linear driver mechanism (not shown). The syringe 89 and the linear driver mechanism are typically referred to as an anticoagulant pump. Anticoagulant from the syringe 89 is introduced into the arterial chamber 56 of the cartridge 42 through a tubing 92 connected to the syringe as shown in FIG. 2. The anticoagulant pump is controlled to deliver the desired amount of anticoagulant during the dialysis treatment by the degree to which the anticoagulant pump moves the plunger 90 into the syringe 89 over a given time period.

Tubings 94 and 96 are respectively connected to the arterial chamber 46 and venous chamber 64 of the cartridge 42 as shown in FIG. 2. Clamps (not shown) are connected to the ends of the tubings 94 and 96 to selectively vent accumulated air from the chambers 46 and 64. An additional tubing 98 is connected to the arterial chamber 46 through which medicines or other additives may be introduced into the blood during treatment.

In addition to these basic components and functionality typically employed in dialysis, the dialysis machine includes conventional input/output ("I/O") devices, such as a touch-screen monitor 84 shown in FIG. 1. Control and safety information is supplied to the dialysis machine 30 by an operator through the monitor 84. Operational and safety information derived from the machine 30 is displayed to the operator at the monitor 84. Other types of I/O devices for use with dialysis machines are also typical.

The safety standards which govern dialysis machines require that the machine must place the patient in a safe state if a malfunction occurs. This safety system functionality can not be disabled or avoided to place the patient in an unsafe condition. The same safety standards also require that the safety system software and functionality must be isolated from the control system software and functionality so that changes in the control system software do not affect the safety system software. The safety capabilities of the dialysis machine are considered to be "validated" once safe operation has been confirmed. The approval to use the dialysis machine is predicated on its validated safety system. Should any change in the safety system software occur, the machine must be re-validated before further use. Re-validation can be an extensive and time-consuming task and is to be avoided if possible. Revalidation can be avoided if it is demonstrated that the safety system software is isolated from the control system software.

The typical approach for controlling dialysis machines, while achieving the dual requirements of recovering into a safe patient state from a malfunction and isolating the safety system functionality from the control system functionality, has been to employ two or more separate microcontrollers with separate memories, and dedicate one of the microcontrollers solely to perform safety system functions and dedicate the other one or more of the microcontrollers solely to performing control system functions. In this manner, the safety system microcontroller should theoretically be able to recover from a failure occurring while the dialysis machine is performing control system functions. Furthermore the separate microcontrollers and their separate software isolates the safety system functionality from the control system functionality, and makes the control system and safety system functionality theoretically independent of each other.

Figure 3:
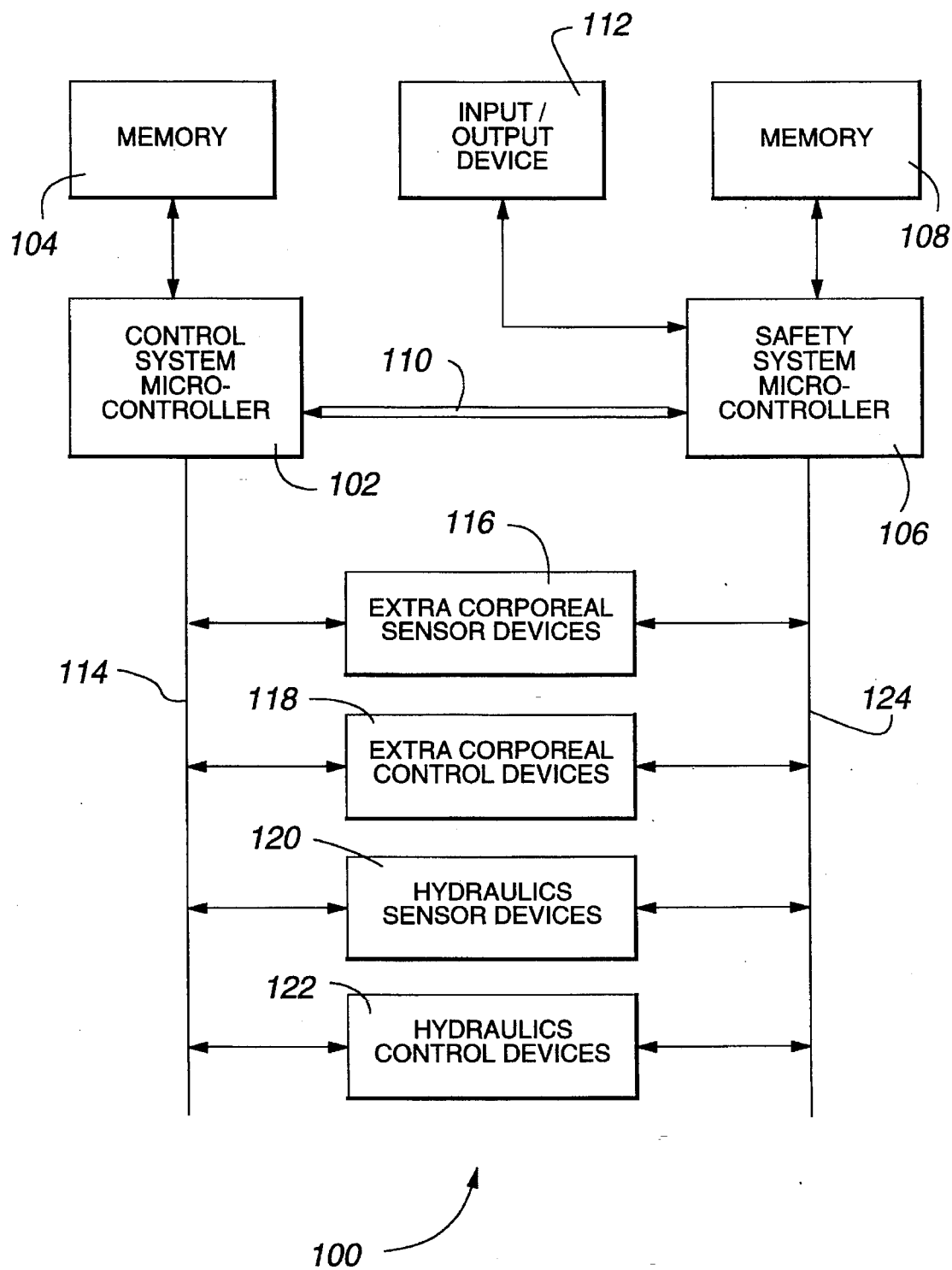
FIG. 3 is a block diagram of a typical prior art two-microcontroller, control system and safety system employed in all presently known prior art dialysis machines.

An example of a prior art control system and safety system control circuit 100 for a prior art dialysis machine is illustrated in FIG. 3. This prior art control circuit 100 utilizes one or more microcontrollers 102 to achieve all of the normal and intended control system functions. Software for accomplishing the control system functions is resident in a control system memory 104 associated only with the control system microcontroller 102. A separate and independent microcontroller 106 performs the safety system functions. The safety system microcontroller 106 operates from safety system software from a safety system memory 108 that is associated only with the safety system microcontroller 106.

One or more conventional Input/Output (I/O) devices 112 are connected to the safety system microcontroller 106 by which to enter and receive information concerning the operation and safety of the dialysis machine. The I/O device 112 and the functionality associated with it is sometimes referred to the operator-machine interface (OMI) system. Since the OMI system must interact with both the safety system and the control system, a bus 110 or network conveys information between the safety system microcontroller 106 and the control system microcontroller 102. The information transferred between the two microcontrollers 102 and 106 includes not only the input information derived from the I/O device 112, but also includes operating information which is supplied at the I/O device by an operator during treatment.

Information entered through the I/O device 112 is received by the safety system microcontroller 106, where the relevant actions are taken, including recording the relevant input information in the memory 108. By applying the input information directly to the safety system microcontroller 106, there is a minimal likelihood that the input information could be corrupted during the information entry process. Furthermore the safety system microcontroller 106 directly confirms the information which has been entered back to the operator, thereby avoiding the possibility of intervening corruption of the entered information or the information confirmed back to the operator. The direct interaction of the input information with the safety system microcontroller is also a requirement of the safety standards.

The control system microcontroller 102 is connected by a control system bus 114 to various extracorporeal flow path sensor devices 116, to various extracorporeal flow path control devices 118, to various sensor devices 120 and control devices 122 associated with the hydraulics flow path (FIG. 2). The devices 116, 118, 120 and 122 are the typical ones employed in dialysis machines, some of which have generally been described in conjunction with FIG. 2 above.

The extracorporeal sensor devices 116 derive signals representative of the rate of volumetric flow through the arterial line 38, the operational characteristics of the arterial blood pump 34, the rate of volumetric flow through the venous line 66, the operational characteristics of the venous blood pump, and the amount of air, if any, in the venous line 66 as sensed by the air detector 70, the temperature and pressure of the blood at various points throughout the extracorporeal blood flow path, among other typical extracorporeal parameters. The extracorporeal control devices are those which control the flow of blood through the extracorporeal flow path and control other effects in the extracorporeal blood flow path. Extracorporeal control devices include the arterial blood pump 34, the venous blood pump, the arterial clamp 40, the venous clamp 72, and the anticoagulant pump, among other typical dialysis control devices.

The hydraulics sensor devices 120 derive signals representative of the amount of dialysate available in the supply 76, the rate of volumetric flow through the dialysate supply line 78, the operational characteristics of the dialysate pump 74, the temperature of the dialysate entering the dialyzer 54, the conductivity of the dialysate, the relative pressure across the medium 56 in the dialyzer 54, the volumetric flow rate of the dialysate in the dialysate waste line 82, and the operational characteristics of the drain pump 84, among other typical hydraulics flow path parameters. The hydraulics control devices include the dialysate pump 74, the heater 80, and the drain pump 84, among others.

The safety system microcontroller 106 is also connected to the extracorporeal sensor and control devices 116 and 118, and the hydraulics sensor and control devices 120 and 122. However the safety system microcontroller 106 is connected to these elements by its own safety system bus 124.

The separate control system and safety system buses 114 and 124 achieve isolation and redundancy between the management and safety systems. If the control system microcontroller 102 and its associated elements should experience a catastrophic failure or other malfunction, the safety system microcontroller 106 is likely to remain unaffected and will therefore be in a condition to place the entire dialysis machine into a safe patient state by directly controlling the devices 118 and 122. The safety system microcontroller 106 can directly exercise safety functions over the dialysis machine. Generally, a safe patient state will be achieved by closing one or more of the blood clamps 40 and 72, stopping the operation of the arterial blood pump 34 (and venous blood pump, if used), and bypassing the flow of dialysate from the dialyzer 54 by changing the state of the bypass valves 87 to directed the dialysate away from the dialysate chamber 60. On the other hand, if the safety system microcontroller experiences a failure or other malfunction, the control system microcontroller 102 is capable of detecting such a failure or malfunction and immediately placing the dialysis machine in a safe patient state.

While the typical prior art control circuit 100 is effective in obtaining the desired control system and safety system functionality, there is a considerable amount of hardware and software redundancy within it. This redundancy adds to the cost of the dialysis machine. Although the added costs attributable to this redundancy are apparent, an approach to eliminating the redundant components while still meeting the safety and governmental standards has not been apparent until the advent of the present invention.

Figure 4:
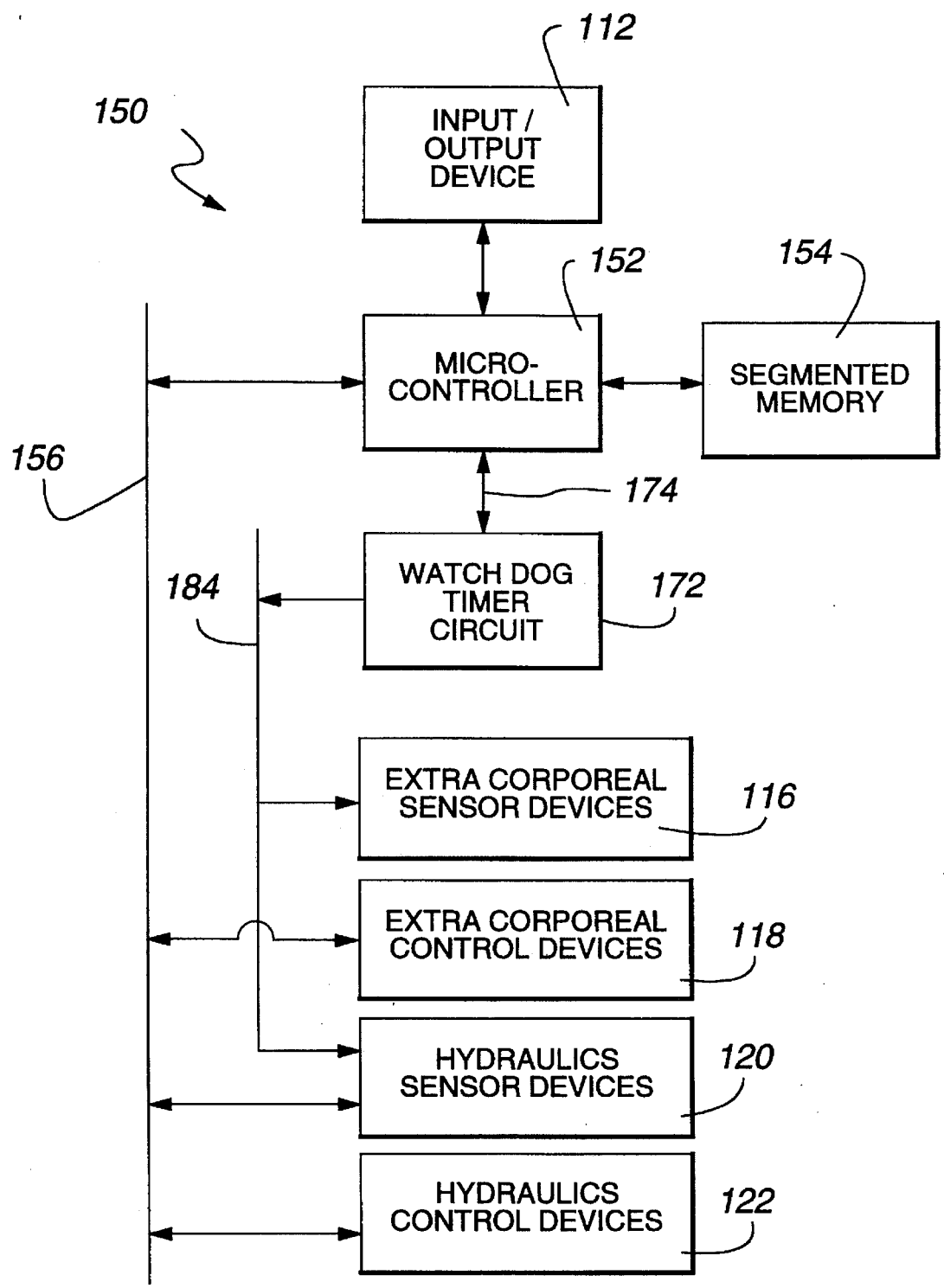
FIG. 4 is a block diagram of a single microcontroller control system and safety system of the present invention which is incorporated in the dialysis machine shown in FIG. 1.

A single microcontroller control system and safety system for a dialysis machine which satisfies present safety standards is shown at 150 in FIG. 4. The system 150 utilizes a single microcontroller 152 to which a segmented memory 154 is connected. The memory 154 contains the safety system software and the control system software. The single microcontroller 152 executes both the safety system functionality and the control system functionality by access to and use of the code recorded in the memory 154.

The I/O devices 112 enter information into and obtain information from the single microcontroller 152. An excellent technique for validating the entry and authenticity of the entered information is described in the above mentioned application for an information Entry Validation System and Method for a Dialysis Machine.

The typical extracorporeal sensor and control devices 116 and 118, respectively, and the typical hydraulics sensor and control devices 120 and 122, respectively, are connected to the microcontroller 152 by a network 156. The network 156 communicates signals between the microcontroller 152 and the sensor and control devices 116, 118, 120 and 122. The microcontroller 152 receives sensor signals from the sensor devices 116 and 120 and processors this information using the control and safety system software. Control signals are generated by the microcontroller 152 and delivered to the control devices 118 and 120 to control the operation of the dialysis machine.

The microcontroller 152 is preferably one with an embedded protected mode processor. Embedded protected mode operation is currently only available in a few microprocessors. However, the concept can be applied to any general purpose microprocessor or microcontroller by writing the specific software. In general, protected mode operation involves the ability to save a state vector when a context switch occurs. A context is the term of computer science typically applied to describe one of a number of different operational states of a computer system. A context switch refers to the transfer of control of the CPU (central processing unit) from one operational task to another operational task. A state vector is a term of computer science which relates to all of the registers, interrupts, privilege levels and other information necessary to define and regain the point in the instructional code of a program where a context switch occurred. By saving the state vector, the previous operating task can be regained as it existed prior to the context switch, if it is desired to do so.

The protected mode functionality is particularly advantageous in dialysis machines. The ability to save the state vector assures the ability of the single microcontroller to recover into a safe patient state in safety system functionality if a malfunction in the control system or operating system functionality occurs. The protected mode functionality satisfies the one safety requirement that the dialysis machine have the capability to recover into a safe patient state. Currently available processors which use protected mode functionality are the 386 and 486 based general purpose microprocessors and the 386EX microcontroller supplied by Intel.

The single microcontroller 152 utilizes a real time operating system (RTOS) in conjunction with the protected mode functionality. The RTOS will recover the state vector from a failure in an operating state or context. If the RTOS is affected by the failure, the embedded processor functionality of the single microcontroller 152 has the inherent capability of recovering the state vector.

Figure 5:
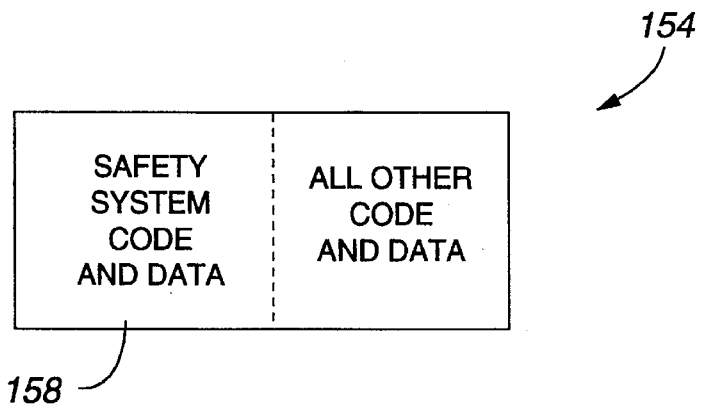
FIG. 5 is an illustration of the separation of the safety system software and the other system software in the segmented memory shown in FIG. 4.

The segmented memory 154 separates the safety system software or code and data 158 from all of the other system software or code and data, as is illustrated in FIG. 5. The code in the segmented memory 154 is accessible only from certain contexts. In the case of the dialysis machine and the segmented memory 154 shown in FIG. 5, the safety system software and data 158 is accessible only from the safety system context and the RTOS context. Thus any attempt to gain access to the safety system code and data 158 from a context other than the safety system or the RTOS will be prohibited. By using the segmented memory 154 in this manner, the safety system software and data 158 will not be inadvertently modified while the system is operating in the control system context.

The separation obtained by the segmented memory 154 protects the validation of the safety system functionality without requiring re-validation each time the control system software is modified. Without this separation it would be difficult to employ a single microcontroller in a manner which is cost effective from the validation standpoint, because software updates to the control system are commonplace. Use of a segmented memory is a conventional technique of isolating programs within a computer memory and allowing access to those programs only from certain specifically-defined contexts.

The capability to achieve context switches between the safety system, the control system and all of the other systems in the dialysis machine is governed by privilege, which is discussed in connection with FIG. 6. The RTOS, designated at 160 in FIG. 6, executes the most basic functionality of the microcontroller 152, and therefore must have overall control over the entire dialysis machine. The RTOS therefore has the highest level of privilege and can access any portion of the segmented memory.

The safety system software 158 has the next lesser level of privilege, because the safety system software must be able to access the safety system code and data 158. The control system software 162, the extracorporeal system software 164, the hydraulics system software 166, the other miscellaneous software 168 and the OMI system software have the next lesser level of privilege.

With the three levels of privilege to the software, the RTOS has control over any of the systems within the dialysis machine at any time, because the RTOS can access any location in the memory. However, it is not desirable for the RTOS to access any location, only those locations necessary to achieve context switches. The safety system controls itself due to its access rights to the safety software and data in the memory, and has the right to control the other systems in the dialysis machine due to its access rights to all of the other systems software. The other systems at the lowest level of privilege can access their own programs, but can not access the safety system software or the RTOS.

By employing the software architectural privilege hierarchy, the RTOS always has control over those tasks which are currently executing. As such, combined with the protected mode of operation of the microcontroller, the state vector can be recovered under malfunctions and errors. Recovery of the state vector allows the safety system software to place the dialysis machine into a safe patient state. The control system software has access to all of the remaining dialysis machine functionality, as needed to perform proper control. The OMI system interacts directly with both the safety system and the control system. The extracorporeal, hydraulics and other systems generally interact with the control system. Access to these other systems by the safety system or the OMI system is usually but not always through the control system.

The safety and control system 150 also protects against the catastrophic failure of even the microcontroller 152, as is shown in FIG. 4. The system 150 employs a conventional watchdog timer circuit 172 which is connected to the microcontroller 152. The watchdog timer circuit 172 operates in the conventional manner by timing the interval between periodic signals supplied by the microcontroller at 174. The periodic receipt of the signals 174 from the microcontroller indicates that the microcontroller is operating properly. Should the watchdog timer circuit 172 fail to receive the periodic signals within the expected time interval(s), the failure of the microcontroller 152 is indicated. The watchdog timer circuit 172 responds by delivering a control signal to the extracorporeal control devices 118 and the hydraulics control devices 122. The control signal effectively de-energizes the control devices 118 and 122 to cause the dialysis machine to assume the safe patient state. As previously indicated, the safe state involves closing the arterial and venous clamps 40 and 72, stopping the arterial blood pump 34 and the venous blood pump, and bypassing the flow of dialysate around the dialyzer by changing the state of the bypass valves 87. A reset signal to the microcontroller which will effectively achieve the safe patient state.

Because the circuitry in the watchdog timer circuit 182 and the relevant circuitry in the control devices is generally logic or hard-wired discrete circuitry, it does not depend on the operation of a processor or software to achieve its functionality. The simplicity and reliability of these hard-wired elements achieve a high level of reliability in performing the fail-safe function of placing the dialysis machine in a safe patient state.

Figure 6:
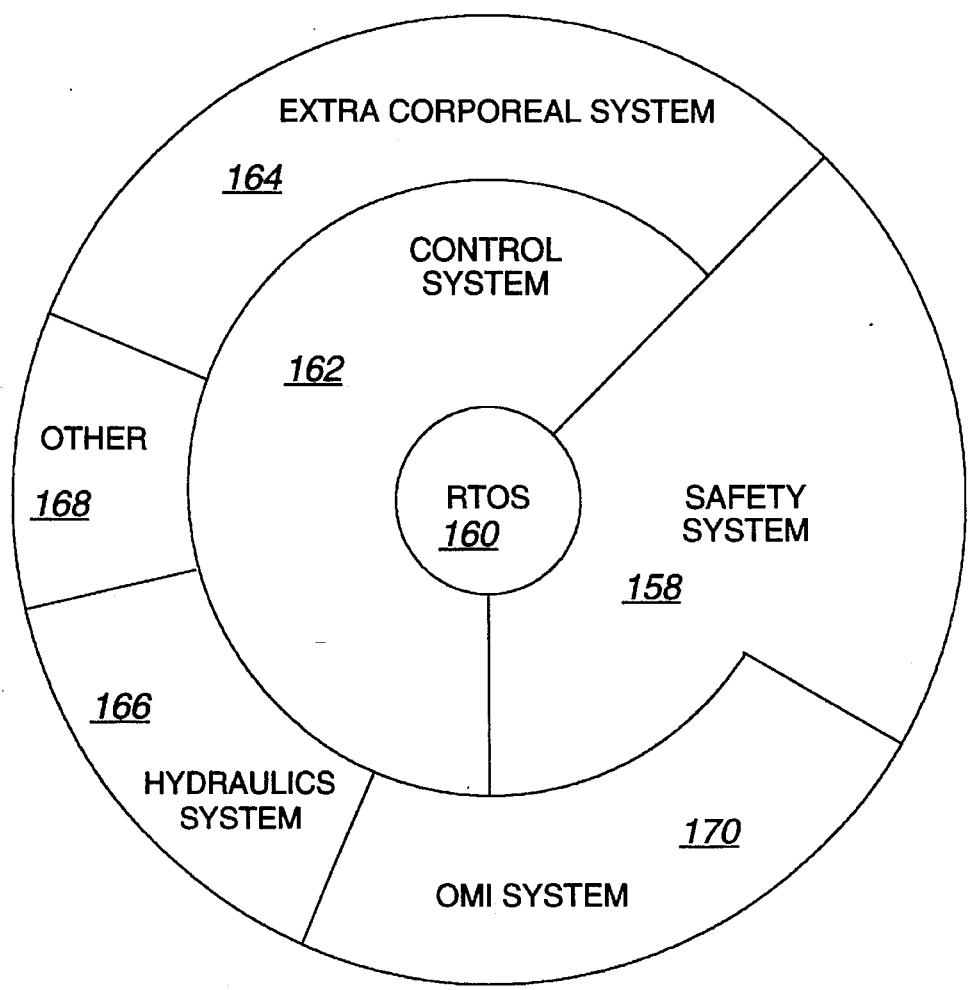
FIG. 6 is an illustration of the interrelationship of the software employed in the single microcontroller control system circuit shown in FIG. 4.

Organizing the software into hierarchical privilege levels shown in FIG. 6 assures both efficient operation of the dialysis machine and compliance with the available safety regulations. The software privilege hierarchy assures that the RTOS and safety system software 158 will always be able to gain control of the microcontroller and place the dialysis machine in the safe patient state. The segmented memory 154 assures that the safety system software can only be accessed from the safety system or RTOS contexts, and therefore assures that inadvertent changes in the safety system software will not occur when accomplishing control system functionality. Many other advantages and improvements in the field of dialysis machines are also apparent after a complete operation of the present invention.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A dialysis machine comprising a single microcontroller having a connected segmented memory operative for solely executing safety system instructional code and control system instructional code to perform respectively substantially all safety system functions and control system functions of the dialysis machine during dialysis treatments.

2. A dialysis machine comprising a single microcontroller having a single memory in which control system and safety system instructional code are separately recorded in isolation from one another, the microcontroller operative for executing safety system instructional code and control system instructional code to perform respectively substantially all safety system functions and control system functions of the dialysis machine during dialysis treatments.

3. A dialysis machine comprising:

a single microcontroller operative for performing safety system and control system functions, and a single memory connected to the single microcontroller in which there is recorded a control system instructional code, a safety system instructional code and an operating system instructional code, and wherein:

the single microcontroller is operative for executing the safety system instructional code and the control system instructional code to perform respectively substantially all of the safety system and control system functions of the dialysis machine during dialysis treatments, the single memory is a segmented memory, the safety system instructional code is recorded in the segmented memory separately from and in isolation from the control system instructional code, the safety system instructional code can be accessed only when the microcontroller is executing one of the safety system code or the operating system code, and the safety system instructional code can not be accessed when the microcontroller is executing the control system instructional code.

4. A dialysis machine comprising:

a single microcontroller operative for performing safety system and control system functions, a segmented memory connected to the single microcontroller in which there is recorded a control system instructional code and a safety system instructional code, the single microcontroller is operative for executing safety system instructional code and control system instructional code to perform respectively substantially all of the safety system and control system functions of the dialysis machine during dialysis treatments, and a watchdog timer circuit connected to the single microcontroller and operative to detect signals indicative of proper functionality of the microcontroller and to place the dialysis machine into a safe patient condition upon the failure to detect signals indicative of proper microprocessor functionality.

5. A dialysis machine as defined in claim 4 wherein the watchdog timer circuit does not include a processor control device.

6. A dialysis machine as defined in claim 5 wherein the single microcontroller sends a periodic signal to the watchdog timer circuit, and the watchdog timer circuit detects proper functionality of the microcontroller by the receipt of the periodic signal.

7. A dialysis machine comprising:

a single microcontroller operative for performing safety system and control system functions, a memory connected to the single microcontroller in which there is recorded a control system instructional code, a safety system instructional code and a real time operating system (RTOS) instructional code, and wherein:

the single microcontroller is operative for executing the safety system instructional code and the control system instructional code to perform respectively substantially all of the safety system and control system functions of the dialysis machine during dialysis treatments, the single microcontroller also executes the RTOS instructional code while performing the control system and safety system functions, and the single microcontroller is operative in a protected mode of operation.

8. A dialysis machine as defined in claim 7 wherein the single microcontroller has an embedded processor.

9. A dialysis machine as defined in claim 7 wherein the ROTS instructional code has a privilege to access the control system instructional code and the safety system instructional code, and the safety system instructional code has a privilege to access the control system instructional code.

10. A dialysis machine as defined in claim 9 wherein the protected mode of operation allows recovery of a state vector upon a failure in execution of the RTOS instructional code and the control system instructional code and the safety system instructional code, and the RTOS instructional code allows recovery of a state vector upon a failure in execution of the control system instructional code.

11. A dialysis machine as defined in claim 10 further comprising a segmented memory in which instructional code for the safety system is recorded separately from and in isolation from instructional code for the control system, and the instructional code for the safety system can be accessed only when the microcontroller is executing safety system or operating system functions.

12. A dialysis machine as defined in claim 11 further comprising a watchdog timer circuit connected to the single microcontroller and operative to detect a failure of the microcontroller and to place the dialysis machine into a safe patient condition upon the failure of the microcontroller.

13. A dialysis machine for performing safety system functions and system control functions during the performance of a dialysis treatment, comprising:

a single microcontroller having a real time operating system (RTOS) to execute RTOS functions and by which to execute instructional code to perform the safety system functions and the control system functions during dialysis treatment;

the microcontroller having an embedded processor with a protected mode of operation to recover a sate vector upon a failure occurring during the execution of the RTOS functions and the safety system functions and the control system functions;

the RTOS having the capability to recover a state vector upon a failure occurring during the execution of the safety system functions and control system functions;

a segmented memory connected to the microcontroller having segments in which instructional code defining the safety system functions is recorded separately and in isolation from the code defining the control functions; and the RTOS functions and the safety system functions each having a privilege to access the segment of the segmented memory containing the code defining the safety system functions, and the control system functions do not have a privilege to access the segment of the segmented memory containing the code defining the safety system functions.

14. A dialysis machine as defined in claim 13 further comprising:

a watchdog timer circuit connected to the single microcontroller, the watchdog timer circuit being operative to detect a failure of functionality of the microcontroller and to place the dialysis machine into a safe patient condition upon detection of a failure of the microcontroller.

15. A dialysis machine as defined in claim 14 wherein the watchdog timer circuit does not include a processor control device.

16. A method of operating a dialysis machine during a dialysis treatment, comprising the steps of:

recording instructional code for use by a single microcontroller in a segmented memory;

isolating the instructional code defining safety system functions and safety data in a first portion of the segmented memory;

isolating the instructional code defining control system functions and control data in a second portion of the segmented memory;

executing the instructional code for the safety system functions on the microcontroller to perform safety system functions;

executing the instructional code for the control system functions on the microcontroller to perform control system functions;

executing the instructional code of a real time operating system (RTOS) on the microcontroller during execution of the instructional code for the safety system and control system functions;

including within the RTOS instructional code a capability to recover a state vector upon a failure in the execution of the instructional code for one of the safety system functions or the control system functions;

employing a protected mode of operation in the microcontroller to recover a state vector upon a failure in the execution of the instructional code of the RTOS and the safety system and the control system; and accessing the segmented memory to retrieve the instructional code and data for the safety system functions only when the microcontroller is operating in one of a safety system or an RTOS context.

\* \* \* \* \*